US00PP24140P3

(12) United States Plant Patent
Slaughter et al.

(10) Patent No.: US PP24,140 P3
(45) Date of Patent: Jan. 7, 2014

(54) NECTARINE TREE, 'BURNECTTWENTYFIVE'

(50) Latin Name: ***Prunus persica* (subspecies *nucipersica*).**
Varietal Denomination: Burnecttwentyfive

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 112 days.

(21) Appl. No.: 13/374,254

(22) Filed: Dec. 19, 2011

(65) Prior Publication Data

US 2013/0160172 P1 Jun. 20, 2013

(51) Int. Cl.
*A01H 5/00* (2006.01)

(52) U.S. Cl.
USPC ..... Plt./190

(58) Field of Classification Search
USPC ..... Plt./190
See application file for complete search history.

*Primary Examiner* — June Hwu
(74) *Attorney, Agent, or Firm* — Paine Hamblen, LLP

(57) ABSTRACT

A new and distinct variety of nectarine tree (*Prunus persica* sub species *nuciperisica*), denominated varietally as 'Burnecttwentyfive', and which produces an attractively colored firm-fleshed, acid, clingstone nectarine, which is mature for harvesting and shipment approximately July 14 to July 21 under ecological conditions prevailing in the San Joaquin Valley of central California.

1 Drawing Sheet

Botanical designation: The present invention relates to a new, novel and distinct variety of nectarine tree, *Prunus persica* (subspecies *nucipersica*).

Varietal denomination: 'Burnecttwentyfive.'

BACKGROUND OF THE NEW VARIETY

The present variety of nectarine tree resulted from an ongoing program of fruit and nut tree breeding. The purpose of this program is to improve the commercial quality of available deciduous fruit and nut varieties, and rootstocks, by creating and releasing promising selections of *Prunus, Malus* and *Juglans* species. To this end we make both controlled and hybrid cross pollinations each year in order to produce seedling populations from which improved progenies are evaluated and selected.

ORIGIN

The seedling 'Burnecttwentyfive' was originated by us from a population of seedlings grown in our experimental orchards located near Fowler, Calif. The seedlings, grown on their own roots, were the result of a controlled cross made in February of 2004 of a seedling of the yellow-fleshed clingstone nectarine tree "Burnectseven" (U.S. Plant Pat. No. 13,589) which was the seed parent, and an unnamed Burchell seedling, E25.071 nectarine tree which was the pollen parent. Within this seedling population one seedling, which is the present variety, exhibited especially desirable characteristics, and was designated as 'N8.068'. This seedling was marked for subsequent observation. After the 2006 fruiting season the new variety of nectarine tree was selected for advanced evaluation and repropagation.

ASEXUAL REPRODUCTION

Asexual reproduction of the new and distinct variety of nectarine tree was accomplished by budding the new nectarine tree to 'Nemared' Rootstock (USDA, non-patented). This was performed by us in our experimental orchard which is located near Fowler, Calif. Subsequent evaluations have shown those asexual reproductions run true to the original tree. All characteristics of the original tree, and its fruit, were established, and appear to be transmitted through succeeding asexual propagations.

SUMMARY OF THE VARIETY

'Burnecttwentyfive' is a new and distinct variety of nectarine tree, which is considered of large size, and which has vigorous growth. This new nectarine tree variety is also a regular and productive bearer of relatively large, firm, acidic, yellow fleshed, melting, clingstone fruit which have good flavor and eating quality. The tree of the present variety displays a medium chilling requirement of approximately 650 hours or more. Still further, the present tree also produces relatively uniformly sized fruit throughout the tree. Additionally, the fruit produced by the present tree has a very high degree of red skin coloration, a firm, yet melting flesh and appears to have good handling and shipping qualities. The 'Burnecttwentyfive' Nectarine tree bears fruit which are ripe for commercial harvesting and shipment on approximately July 14 to July 21 under the ecological conditions prevailing in the San Joaquin Valley of central California. In relative comparison to the seed parent tree ('Burnectseven' U.S. Plant Pat. No. 13,589), the 'Burnecttwentyfive' Nectarine tree produces a nectarine which exhibits 20-40% more external red blush coloration than the seed parent. In relative comparison to the pollen parent tree E25.071, (unpatented) the 'Burnecttwentyfive' nectarine ripens approximately 7-10 days earlier. In addition, the present new nectarine tree produces fruit approximately 3-7 millimeters larger and requires approximately 150 less chill units than the nectarine tree 'Summer Fire' (U.S. Pat. No. 7,506), which is the most similar commercial variety in ripening date known to the breeders at this time. The lower chilling requirement of the present, new variety allows it to produce more flower buds than the nectarine tree 'Summer Fire' (U.S. Pat. No. 7,506), and subsequently the 'Burnecttwentyfive' tree has exhibited the potential to produce larger crops.

BRIEF DESCRIPTION OF THE DRAWING

The accompanying drawing, which is provided, is a color photograph of the new variety of nectarine tree. The photograph depicts two whole mature fruit, and one mature fruit which is dissected substantially in the equatorial plane, and which is seen from the apical perspective. This photograph also reveals the flesh and the stone characteristics thereof. The external coloration of the fruit, as shown, is sufficiently matured for harvesting and shipment. Additionally, the photograph displays a sample vegetative shoot bearing typical leaves; and a typical stone; with the flesh removed.

The colors in the photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society Fourth Edition, 2001) and the descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of nectarine tree, the following has been observed during the sixth fruiting season under the ecological conditions prevailing at orchards located near the town of Fowler, county of Fresno, state of Calif. All major color code designations are by reference to The R.H.S. Color Chart (Fourth Edition, 2001.) provided by The Royal Horticultural Society of Great Britain. Common color names are also occasionally used.

TREE

*Size.*—Generally — Considered medium-large as compared to other common commercial nectarine cultivars ripening in the same season of maturity. The tree of the present variety was pruned to a height of approximately 300.0 cm to about 310.0 cm at maturity. The average spread of the new tree is approximately 4.7 meters when measured during the fifth year of growth.

*Vigor.*—Considered moderately vigorous. The present variety grew from about 150.0 cm to 155.0 cm in height during the first growing season. The new nectarine tree variety was pruned to a height of approximately 140.0 cm during the first dormant season, and primary scaffolds were then selected for the desired tree structure.

*Productivity.*—Productive. The fruit set varies from 1.5 to several times more than the desired crop load. The fruit set is spaced by thinning to develop the remaining fruit into the desired market-sized fruit. The number of the fruit set varies with the prevailing climatic conditions, and the current cultural practices employed during the bloom period. Therefore, this characteristic is not distinctive of this new variety.

*Bearer.*—Regular. Fruit set has been heavy, and significant thinning was necessary during the past 5 growing seasons.

*Form.*—Upright, and pruned into a vase shape.

*Density.*—Considered medium dense. It has been discovered that pruning the branches from the center of the tree to obtain a resulting vase shape allows for proper air movement in the tree, and appropriate amounts of sunlight to enhance fruit color and renewal of fruiting wood throughout the entire tree.

*Hardiness.*—The present tree was grown and evaluated in USDA Hardiness Zone 9. The winter chilling requirements of the new tree are approximately 650 hours at a temperature below 7.0 degrees C. The present variety appears to be hardy under typical Central San Joaquin Valley climatic conditions.

TRUNK

*Diameter.*—Approximately 21.0 cm in diameter when measured at a distance of approximately 15.24 cm above the soil level, on trees which are six years old.

*Bark texture.*—Considered moderately rough, with numerous folds of papery scarfskin being present.

*Lenticels.*—Numerous flat, oval lenticels are present. The lenticels range in size from approximately 4.0 to about 8.0 millimeters in width; and from about 1.0 to about 2.0 millimeters in height. It should be noted that as the bark of the trees mature, the lenticels become less apparent and also less abundant.

*Lenticel color.*—Considered an Orange-Brown, (RHS Greyed-Orange Group 166 D).

*Bark coloration.*—Variable, but it is generally considered to be Grey-Brown, (RHS Greyed-Orange Group 177 A).

BRANCHES

*Size.*—Considered medium-large for the variety.

*Diameter.*—Average as compared to other nectarine tree varieties. The branches have a diameter of about 12.0 centimeters when measured on trees which are six years old.

*Surface texture.*—Average, and appearing furrowed on wood which is several years old.

*Crotch angles.*—Primary branches are considered variable between about 45 to about 54 degrees from the horizontal axis. This particular characteristic is not considered distinctive of the present variety, however.

*Current season shoots.*—Surface texture — Substantially glabrous.

*Internode length.*—Approximately 1.9 to about 2.4 cm. This tree characteristic is highly dependent upon plant vigor influenced by nutrition, soil quality, pruning and tree care and therefore is not particularly distinctive of the new variety.

*Color of mature branches.*—Medium-brown, (RHS Greyed-Orange 177 C).

*Current season shoots.*—Color — yellow green, (RHS Yellow-Green Group N144 A). The color of the new shoot tips is considered a bright and yellow green (RHS Yellow-Green Group 151 D).

LEAVES

*Size.*—Considered medium-large for the species. Leaf measurements have been taken from vigorous, upright, current-season growth, at approximately mid-shoot.

*Leaf length.*—Approximately 135.0 to about 160.0 millimeters.

*Leaf width.*—Approximately 33.0 to about 39.0 millimeters.

*Leaf base shape.*—Slightly oblique relative to the longitudinal axis of the leaf.

*Leaf form.*—Lancelolate.

*Leaf tip form.*—Acuminate.

*Leaf color.*—Upper Surface — Dark green, (approximately RHS Green Group N134 B).

*Leaf texture.*—Glabrous.

*Leaf color.*—Lower Surface — Medium green, (RHS Green Group 143 A).

*Leaf venation.*—Pinnately veined.

*Mid-vein.*—Color. — Light yellow green, (RHS Yellow-Green Group 150 C).

*Leaf margins.*—Generally — Slightly undulating. Form. — Considered crenate, occasionally doubly crenate. Uniformity. — Considered generally uniform.

*Leaf petioles.*—Size. — Considered medium long. Length. — About 7.0 to about 10.0 mm. Diameter. — About 2.0 mm. Color. — Pale green, (RHS Yellow-Green Group 144 B).

*Leaf glands.*—Size. — Considered generally small. About 1.0 mm in height and about 1.0 mm in width. Number. — Generally one per side, occasionally two per side may be found. Rarely glands are absent. Type. — Globose. Color. — Orange brown, (RHS Green Group 137 B). The glands as described herein are described as they would appear during mid-season, but before advancing senescence.

*Leaf stipules.*—Size. — Medium for the variety. Number. — Typically 2 per leaf bud, and up to 6 per shoot tip. Form. — Lanceolate in form, and having a serrated margin. Color. — Green, (RHS Green Group 141 A) when juvenile, but then graduating to a brown color, (RHS Greyed-Red group 178 B) with advancing senescence. The stipules are considered to be early deciduous.

FLOWER

*Flower buds.*—Generally — The floral buds, depending upon the stage of development, are approximately 8.0 millimeters wide; and about 13.0 millimeters long; conic in form; and slightly appressed relative to the bearing shoot.

*Flower buds.*—Color — The bud scales are reddish-brown, (approximately RHS Greyed-Red Group 178 B). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress, and therefore this information is not presently available.

*Date the first bloom was observed.*—Mar. 1, 2009.

*Blooming time.*—Considered early to mid-season in relative comparison to other commercial nectarine cultivars grown in the central San Joaquin Valley. Date of full bloom was first observed on Mar. 9, 2009. The date of bloom varies slightly with the prevailing climatic conditions, and cultural practices which are employed.

*Duration of the bloom.*—Approximately 10 days. This characteristic varies slightly with the prevailing climatic conditions.

*Flower type.*—The variety is considered to have a showy-type flower.

*Flower size.*—Flower diameter at full bloom is approximately 48.0 to about 56.0 millimeters.

*Bloom quantity.*—Considered abundant.

*Flower bud frequency.*—Normally 2 flower buds appear per node. On occasion 1 bud per node may be observed. Stamen count — On average, 35 stamens per flower appear.

*Petal size.*—Generally — Considered large for the species. Length. — Approximately 21.0 to about 23.0 millimeters. Width. — Approximately 17.0 to about 21.0 millimeters.

*Petal form.*—Rotund to slightly ovate.

*Petal count.*—Typically 5.

*Petal texture.*—Glabrous.

*Petal color.*—Somewhat variable from a light pink, (RHS Red-Purple Group 65 B) to a medium pink, (RHS Red-Purple Group N57 D).

*Fragrance.*—Slight.

*Petal claw.*—Form — The claw is considered cuneate in shape; and has a medium size when compared to other varieties. Length. — Approximately 11.0 to about 13.0 millimeters. Width. — Approximately 9.0 to about 11.0 millimeters.

*Petal margins.*—Generally considered variable, from nearly smooth, to moderately undulate.

*Petal apex.*—Generally — The petal apices appear entire with a broad, shallow apical groove.

*Flower pedicel.*—Length. — Considered medium-long, and having an average length of approximately 5.0 to about 6.0 millimeters. Diameter. — Considered average, approximately 2.0 to 3.0 millimeters. Color. — A pale green when bud scales are removed, (RHS Greyed Green Group 195 A).

*Floral nectaries.*—Color. — An orange-brown, (RHS Greyed-Orange Group N172 A).

*Calyx.*—Surface texture. — Generally glabrous. Color. — A dull red, (approximately RHS Greyed-Red Group 178 B).

*Sepals.*—Surface texture. — The surface has a short, fine, pubescent texture. Size. — Average; and ovate in form; approximately 6.0 mm in length; and approximately 4.0 mm in width. Color. — Upper Surface — A dark reddish purple, (approximately RHS Greyed-Purple Group 183 C). Color — Lower Surface — Grey-Brown (RHS N199B).

*Anthers.*—Generally. — Large in size. Color. — Red to reddish-purple, (approximately RHS Orange-Red Group 32 A) prior to dehistance.

*Pollen production.*—Pollen is abundant, and has a yellow color, (approximately RHS Yellow Group 11 A).

*Filaments.*—Size. — Variable in length, approximately 14.0 to about 17.0 millimeters in length. Color. — Considered a pale pink, (RHS Red-Purple Group 63 C) at maturity.

*Pistil.*—Number. — Normally 1, very rarely 2. Generally. — Average in size. Length. — Approximately 19.0 to about 21.0 millimeters including the ovary. Color. — Considered a very pale green, (approximately RHS Yellow-Green Group 144 D). Surface Texture. — The variety has a long glabrous pistil.

FRUIT

*Maturity when described.*—Firm ripe condition (shipping ripe). Date of first picking. — Jul. 14, 2009 Date of last picking. — Jul. 21, 2009. The date of harvest varies slightly with climatic conditions.

*Size.*—Generally — Considered large, and uniform.

*Average cheek diameter.*—Approximately 68.0 to about 71.0 millimeters.

*Average axial diameter.*—Approximately 71.0 to about 73.0 millimeters.

*Typical weight.*—Approximately 255.0 grams. This characteristic is highly dependent upon the prevailing cultural practices, and therefore is not particularly distinctive of this new variety.

*Fruit form.*—Generally — Rounded to slightly elongated through its axis. The fruit is generally uniform in symmetry.

*Fruit suture.*—Shallow, and extending from the mid-equatorial region to the apex. No apparent callousing or stitching exists along the suture line.

*Suture.*—Color — The background color appears to be a medium yellow, (approximately RHS Yellow-Orange Group 16 B), with some occasional red coloration, (approximately RHS Red Group 42 A).

*Ventral surface.*—Form — Often lobed in one hemisphere.

*Apex.*—Shape — Rounded.

*Base.*—Shape — Slightly retuse.

*Stem cavity.*—Shape — Rounded and relatively shallow. The average depth of the stem cavity is about 1.0 cm. The average width of the stem cavity is about 2.8 cm.

*Fruit skin.*—Thickness. — Considered medium in thickness; and tenacious to the flesh. Texture. — Glabrous. Taste. — Slight astringency is noted. Tendency to crack. — Cracking has not been observed. Russeting has not been observed to date on the oldest bearing trees.

*Blush color.*—The blush color is variable from a medium red, (approximately RHS Orange-Red Group N34 B) to a dark red, (approximately RHS Orange-Red Group N34 A). Blush color ranges from approximately 70% to about 85% of the fruit surface depending upon the sunlight exposure and prevailing growing conditions.

*Ground color.*—Generally a light yellow, (approximately RHS Yellow-Orange Group 15 B).

*Fruit stem.*—Moderate in length, approximately 6.0 to about 8.0 millimeters. Diameter. — Approximately 2.0 to about 3.0 millimeters. Color. — Light tan, (approximately RHS Greyed-Orange Group 164 D).

*Flesh.*—Ripens. — Evenly. Texture. — Firm, and dense. Considered melting. Fibers. — Few, small, and tender ones are typically found. Aroma. — Slight. Eating Quality. — Considered good. Flavor. — Considered sweet and acidic. The flavor is considered pleasant. Juice. — Moderate. Brix. — About 14.5 degrees. This characteristic varies slightly with the number of fruit per tree; the prevailing cultural practices; and the surrounding climatic conditions. Flesh Color. — Yellow-orange, (approximately RHS Yellow-Orange Group 16 A). As maturity increases a reddish pigmentation (approximately RHS Red Group 46 B) develops. This pigmentation can increase until a majority of the fruit flesh develops a substantial degree of red coloration.

STONE

*Type.*—Clingstone.

*Size.*—Considered medium for the variety. The stone size varies with the resulting crop load, and tree vigor, and is therefore is not considered a distinguishing characteristic of this new variety.

*Length.*—Average, about 27.0 to about 31.0 millimeters.

*Width.*—Average, about 22.0 to about 25.0 millimeters.

*Diameter.*—Average, about 17.0 to about 22.0 millimeters.

*Form.*—Obovoid.

*Base.*—The stone is slightly oblique relative to the stone's vertical axis.

*Apex.*—Shape — The stone apex has a small acute tip.

*Stone surface.*—Surface Texture. — Substantial pitting is evident, in general, from the base past the equatorial plane. Grooving is usually observed along the pit margin near the tip and on the ventral side. Ridges. — Texture — The surface texture varies from sharp to rounded. Ventral edge. — Width — Considered medium, and having a dimension of approximately 3.0 to about 4.0 millimeters when measured at mid-suture. Dorsal Edge. — Shape — Full, heavily grooved, and having relatively smooth edges.

*Stone color.*—The color of the dry stone is a dull red approximately (RHS Greyed-Red Group 181 B).

*Tendency to split.*—Rarely splits have been noted.

*Kernel.*—Generally — The kernel is considered mature at fruit ripening dates. Form. — Considered ovoid. Kernel Size — Approximately 8.0 to 11.0 mm in length; approximately 5.0 to 8.0 mm in width; and approximately 3.5 to 5.0 mm in thickness. Pellicle. — Slightly pubescent. Color. — Considered to be a pale brown (Greyed-Group Group 164 A).

*Use.*—The new variety 'Burnecttwentyfive' is considered to be a Nectarine tree which matures early in the season, and which produces fruit, which are considered firm, attractively colored, and which are useful for both local and long distance shipping.

*Keeping quality.*—Appears excellent. Fruit has stored well for up to 25 days after harvest at 1.0 degree Celsius.

*Shipping quality.*—Good. The fruit of the new nectarine tree variety showed minimal bruising of the flesh, or skin damage, after being subjected to normal harvest and packing procedures.

*Resistance to insects and disease.*—No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by Plant Letters Patent is:

1. A new distinct variety of nectarine tree, substantially as illustrated and described, and which is characterized principally as to novelty by producing an attractively colored, firm-fleshed, acid, clingstone nectarine which is mature for harvesting and shipment approximately July 14 to July 21 under the ecological conditions prevailing in the San Joaquin Valley of central California.

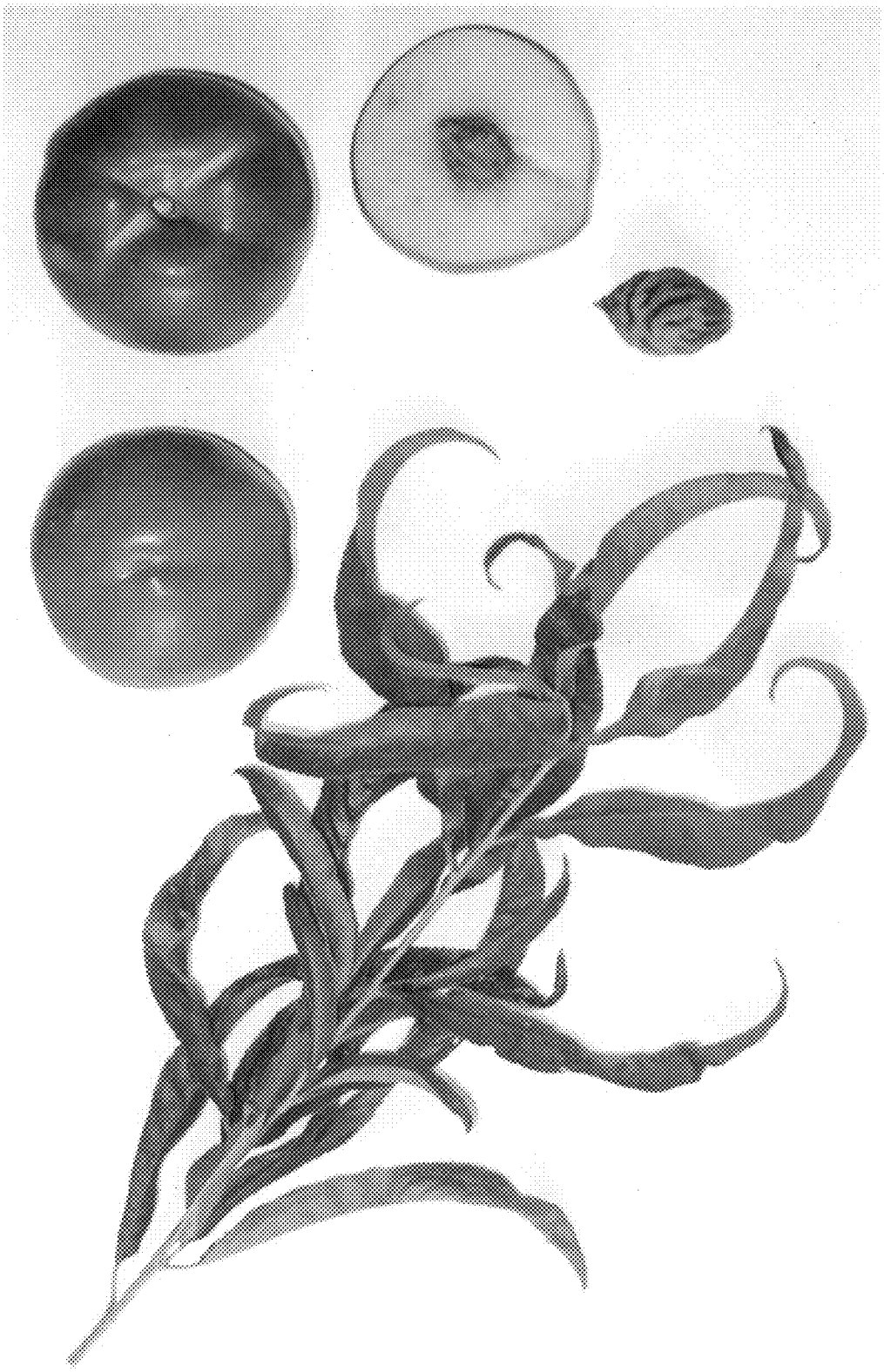

* * * * *